United States Patent [19]

Ball et al.

[11] Patent Number: 4,919,738
[45] Date of Patent: Apr. 24, 1990

[54] DYNAMIC MECHANICAL BONDING METHOD AND APPARATUS

[75] Inventors: W. Kenneth Ball; David J. K. Goulait; James E. Zorb, all of Cincinnati, Ohio

[73] Assignee: The Procter & Gamble Company, Cincinnati, Ohio

[21] Appl. No.: 357,373

[22] Filed: May 25, 1989

Related U.S. Application Data

[63] Continuation of Ser. No. 64,896, Jun. 19, 1987, Pat. No. 4,854,984.

[51] Int. Cl.$^5$ .................... B29C 65/18; B32B 31/20
[52] U.S. Cl. .................... 156/73.5; 156/290; 156/308.4; 156/324; 156/553; 156/555; 156/582
[58] Field of Search ............ 156/73.5, 290, 308.4, 156/324, 553, 555, 582, 583.1; 100/93 RP

[56] References Cited

U.S. PATENT DOCUMENTS

| | | | |
|---|---|---|---|
| 3,081,212 | 3/1963 | Taylor Jr. et al. | 156/164 |
| 3,490,972 | 1/1970 | Rogers | 156/582 |
| 3,530,023 | 9/1970 | Schutte et al. | 156/290 |
| 3,854,031 | 12/1974 | Keller | 219/244 |
| 4,035,219 | 7/1977 | Cumbers | 156/290 |
| 4,106,167 | 8/1978 | Luc | 29/33 |
| 4,144,110 | 3/1979 | Luc | 156/73.5 |
| 4,248,878 | 11/1985 | Evans et al. | 428/95 |
| 4,430,148 | 2/1984 | Schaefer | 156/580.2 |
| 4,605,458 | 8/1986 | Nakamura | 156/324 |
| 4,620,895 | 11/1986 | Kato | 156/290 |
| 4,749,423 | 6/1988 | Vaalburg et al. | 156/290 |

Primary Examiner—Michael Wityshyn
Attorney, Agent, or Firm—Thomas J. Slone; Larry L. Huston; Frederick H. Braun

[57] ABSTRACT

A method of and apparatus for dynamically mechanically bonding together a plurality of laminae, at least one of which comprises thermoplastic material: for example, polyethylene. In one aspect of the invention the laminae are forwarded in face to face relation through a pressure biased nip between a patterned nip defining member and an opposing nip defining member (e.g., a relief patterned cylinder and an anvil cylinder) which members are independently driven to maintain a predetermined surface velocity differential between them. In another aspect of the invention which is particularly useful at intermediate and higher line velocities—preferably for line velocities of about 300 feet or more per minute and, more preferably, for line speeds of about 450 feet or more per minute—the nip defining members may be operated with equal surface velocities. In each of these aspects of the invention, the members may be biased towards each other to provide a predetermined pattern-element-psi loading; and, additionally, they may be independently heated to provide each with an elevated surface temperature which is, preferably, in a predetermined range below the melt temperature of the thermoplastic lamina disposed closet to or in contact with each respective nip defining member as the laminae are forwarded through the nip.

9 Claims, 2 Drawing Sheets

DYNAMIC MECHANICAL BONDING METHOD AND APPARATUS

This is a continuation of application Ser. No. 07/064,896, filed on June 19, 1987, now U.S. Pat. No. 4,854,984.

FIELD OF THE INVENTION

The invention pertains to methods of and apparatus for autogenously (ie, without adhesives) laminating plural layers or laminae of sheet material together, at least one layer of which is thermoplastic film or web or non-woven or the like. It is, however, not intended to thereby limit the invention to precluding adhesive augmentation of such autogenous laminating.

BACKGROUND ART

Laminated Sheet Material And Methods Of Making Such Material are disclosed in U.S. Pat. No. 3,530,023 which issued Sept. 22, 1970 to R. W. Schutte et al. As disclosed, such material comprises at least two adjacent layers of cellulosic fiber sheet material, and a layer of thermoplastic material which layers are secured together at a plurality of bonding areas by heat and pressure without the addition of any adhesive material. This patent states that such bonding may be achieved by forwarding the layers through a nip between two rolls which rolls are arranged to maintain a fixed spacial relationship relative to each other. As further disclosed, one of the rolls may be smooth surfaced with the other having spaced projections extending outwardly from its cylindrical surface; or both rolls may have such projections. Bonding areas of a size of from about 0.0005 to about 0.002 square inches (from about 0.003 to about 0.013 square centimeters) are said to be preferred.

A non-woven structure, method and apparatus for producing non-wovens is disclosed in U.S. Pat. No. 4,035,219 which issued July 12, 1977 To David Charles Cumbers. In this apparatus as disclosed, a thermoplastic non-woven is first formed as by extruding the thermoplastic from a spinneret; and then passing the filamentary mass through bonding means. In the bonding means, a bonding member such as a roll is provided which has projections on it; the bonding member is heated to a temperature below the softening point of the thermoplastic to be bonded, and the bonding member is pressure biased towards a backing member such as a roll; and the material to be bonded is passed therebetween. For example, through the nip between a pair of pressure biased nip rollers: a heated pattern roller having projections; and a backing roller. Bonding is said to be effected by virtue of the work done by the pressure biased, heated projections to compress the material. Projections having areas of from about 0.00001 to about 0.005 square inches (from about 0.00006 to about 0.003 square centimeters) are stated to be preferred albeit projections having areas of up to about 0.001 square inches (about 0.006 square centimeters) are claimed.

While prior art laminating apparatuses and methods for laminating web materials together have addressed some of the problems of achieving such lamination in the absence of adhesives, they have not addressed the problems to the extent of or in the manner of the present invention. For example, and without intending to thereby limit the scope of the present invention, providing an apparatus wherein laminating is achieved through the use of pressure biased laminating rolls which are operated with a predetermined surface velocity differential between them as provided by one aspect of the present invention; and providing an apparatus having heated, velocity method laminating members having pattern elements having areas of greater than 0.002 square inches (about 0.013 square centimeters) which apparatus is particularly useful at intermediate and high line velocities as is provided by another aspect of the present invention.

DISCLOSURE OF THE INVENTION

The invention provides, in one aspect, a method of dynamically bonding plural laminae together, at least one of which laminae comprises thermoplastic material. The method comprises the step of forwarding the laminae through a nip between a patterned nip defining member and a nip defining anvil member. The patterned nip defining member comprises an array of pattern elements. The method further comprises pressure biasing the nip defining members towards each other with a predetermined pattern-element-psi loading; and rotating the nip defining members to provide a predetermined surface velocity differential therebetween. The method may further comprise the step of heating each of the nip defining members to a surface temperature that is a predetermined number of degrees below the melt temperature of the thermoplastic lamina disposed closest to it as the laminae are forwarded through the nip between the nip defining members. Preferably, the nip defining anvil member is smooth surfaced; and is operated at a surface velocity that is greater than the surface velocity of the patterned nip defining member. Additionally, the nip defining members are preferably operated with a surface velocity differential of from about 2 to about 40 percent; and, more preferably, with such surface velocity differential in the range of from about 2 to about 20 percent.

In another aspect of the invention, a method of operating an apparatus for dynamically bonding plural laminae together is provided which assures bonds of high structural integrity in the absence of tearing and the like while assuring longevity of the pattern elements of its patterned nip defining member. Essentially this method entails operating one of the nip defining members at a predetermined velocity: eg, a predetermined line speed in a converting apparatus. Then adjusting the velocity at the other nip defining member and the level of pressure biasing of the nip defining members towards each other to determine an operating point (ie, a desired line velocity at a given velocity differential between the nip defining members and at a given level of nip pressure biasing) at which satisfactory autogenous bonding can be achieved at a level of nip pressure biasing substantially lower than would be required in the absence of a velocity differential between the nip defining members. Preferably, the operating point for each line speed will be at a sufficiently high differential velocity to enable operating at a non-deleterious level of nip biasing pressure to achieve satisfactory bonding: ie, strong bonding in the absence of deleterious tearing or perforating of the laminae. However, at intermediate and high line velocities, operating points may be realized at zero velocity differential: ie, with the nip defining members having equal surface velocities. Generally speaking, non-deleterious levels of nip biasing pressures are pressures below the yield strength of the pattern elements of patterned nip defining members and the like. Such biasing levels assure substantial useful life of the pattern elements disposed on the patterned nip defining member.

In yet another aspect of the invention, an apparatus is provided for dynamically bonding plural laminae together, at least one of which laminae comprises sufficient thermoplastic material to enable dynamically bonding the laminae together: For example, through the application of heat and pressure as opposed to the application of adhesives, bonding agents, and the like. The apparatus comprises a relief patterned nip defining member and a nip defining anvil member that is preferably smooth surfaced; and means for adjustably and controllably pressure biasing the nip defining members together, and operating them at controlled surface velocities and with a controlled surface velocity differential. Preferably, the apparatus further comprises means for independently heating the nip defining members so that the surface temperature of each is within a predetermined range below the melt temperature of whichever lamina of the laminae that comprises thermoplastic material is disposed closest to each respective nip defining member as the laminae are forwarded through the nip defined by the nip defining members.

BRIEF DESCRIPTION OF THE DRAWINGS

While the specification concludes with claims which particularly point out and distinctly claim the subject matter regarded as forming the present invention, it is believed that the invention will be better understood from the following description taken in conjunction with the accompanying drawings in which:

DETAILED DESCRIPTION OF THE INVENTION

Figure 1:
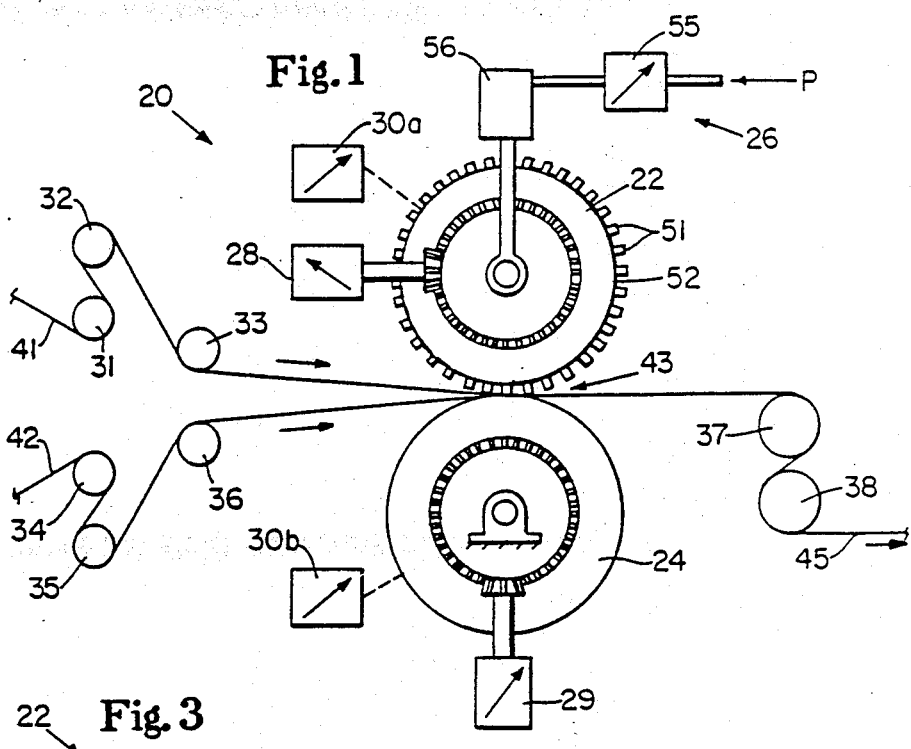
FIG. 1 is a fragmentary, somewhat schematic side elevational view of an exemplary apparatus embodiment of the present invention.

A somewhat schematic, fragmentary side elevational view of a dynamic mechanical bonding apparatus 20 which is an embodiment of the present invention is shown in FIG. 1. Apparatus 20 comprises: patterned cylinder 22; anvil cylinder 24; means 26 for adjustably biasing cylinders 22 and 24 towards each other with a predetermined pressure within a predetermined range of pressures; means 28 and 29 for rotating cylinders 22 and 24, respectively, at independently controlled velocities to provide a predetermined surface velocity differential therebetween; temperature control means 30a and 30b for independently heating cylinders 22 and 24, respectively, to provide predetermined surface temperatures thereon; and rolls 31 through 38. Laminae 41 and 42, and laminate 45 are also shown in FIG. 1. Additionally, apparatus 20 comprises a frame, not shown; and means, not shown, for driving rolls 31 through 38 for controllably forwarding laminae 41 and 42 through the nip 43 defined between cylinder 22 and cylinder 24, and for enabling forwarding the resulting laminate—laminate 45—to downstream apparatus such as a roll winder or web converting apparatus: for example, a disposable diaper converter.

For clarity of the present invention, neither the upstream ends or sources of laminae 41 and 42, nor the downstream destination or user of laminate 45 are shown. However, for example, it is well known to provide laminae of thermoplastic films, and paper and other webs in roll form; and to provide upstream unwinding and splicing means to enable forwarding continuous lengths of such laminae through laminating means and or converters to make products comprising laminated and/or other web elements at controlled velocities and under controlled tension.

Parenthetically, for simplicity and clarity of the invention, apparatus 20 is described herein as comprising cylinders 22 and 24. However, cylinders are but exemplary nip defining members as stated hereinbefore. Accordingly, it is not intended to thereby limit the invention to apparatus comprising cylinders per se. In the same vein, use of the term pattern element is not intended to limit the invention to bonding patterns consisting of only discrete, spaced pattern elements to the exclusion of other patterns: eg, reticulated patterns or patterns comprising continuous or elongate lines of bonding.

Briefly, referring to apparatus 20, FIG. 1, the present invention enables thermolaminating certain laminae together—providing at least one of the laminae comprises sufficient thermoplastic material that is susceptible to being thermobonded to the other laminae—by forwarding the laminae together through a pressure biased nip between a patterned cylinder and an anvil cylinder which cylinders have a predetermined surface velocity difference between them. Such laminating can be effected at substantially lower nip biasing pressure (ie, substantially lower psi loadings on the pattern elements of the patterned cylinder) than if the cylinders are operated at equal surface velocities. Directionally, the greater the surface velocity differential, the lower the required nip biasing pressure. However, too great a surface velocity differential may precipitate tearing of the laminae, or the formation of unwanted holes or perforations therein so should preferably be avoided. Additionally, such laminating may be effected with even lower nip biasing pressure if one or both of the cylinders is heated: preferably to temperatures which are sufficiently lower than the melting points of the laminae that the laminae will not melt or stick to the laminating cylinders in the event, for example, the apparatus is temporarily stopped.

Figure 2:
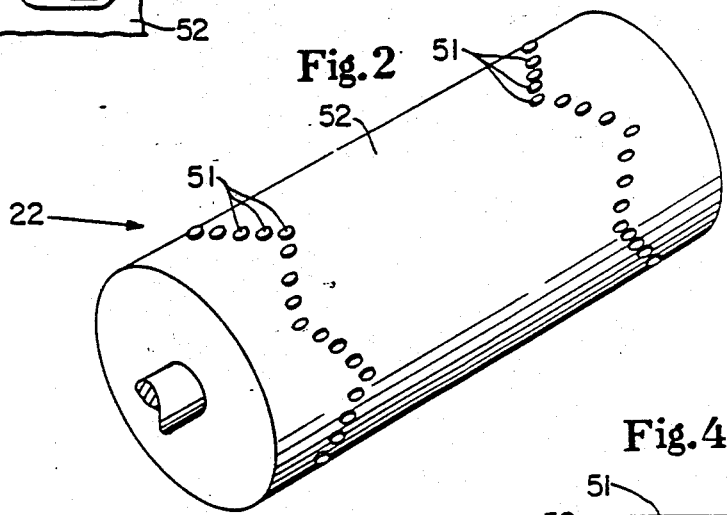
FIG. 2 is a perspective view of the patterned cylinder of the bonding apparatus shown in FIG. 1.
Figure 5:
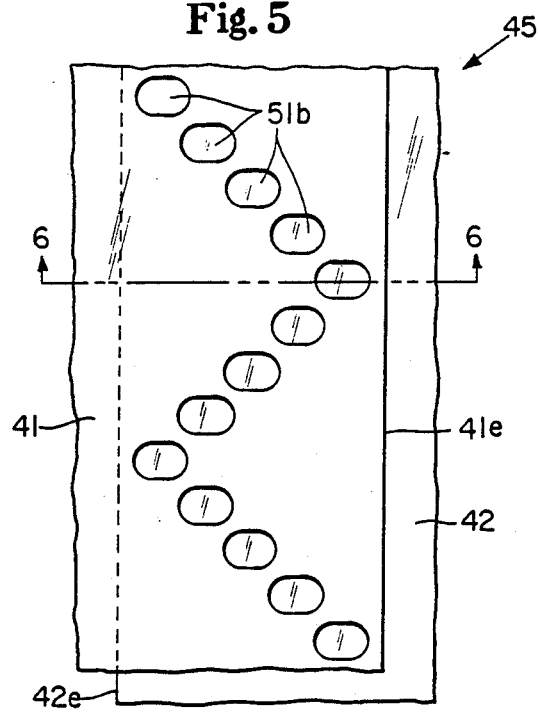
FIG. 5 is an enlarged scale, fragmentary plan view of two laminae having overlapping edge portions bonded together through the use of the present invention.
Figure 6:
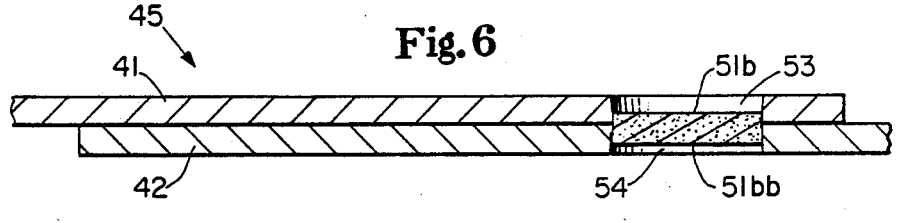
FIG. 6 is a somewhat schematic, fragmentary sectional view taken along section line 6—6 of FIG. 5.
Figure 7:
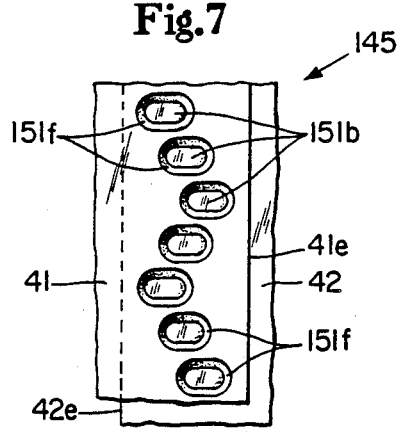
FIG. 7 is an enlarged scale, fragmentary plan view that is similar to FIG. 5 but wherein a different pattern of bonds is shown for lap bonding edge portions of two laminae together through the use of the present invention.

Referring now to FIG. 2, patterned cylinder 22 is configured to have a circular cylindrical surface 52, and a plurality of protuberances or pattern elements 51 which extend outwardly from surface 52. The protuberances are disposed in a predetermined pattern: each pattern element being configured and disposed to precipitate a bond site in the laminate being produced to effect a predetermined pattern of bond sites in the laminate. As shown in FIG. 2, cylinder 22 has a saw-tooth shape pattern of protuberances 51 which extend circumferentially about each end of the cylinder. Such a cylinder is configured, for example, to laminate or lap-seam together a relatively narrow perforated web to each machine direction side edge of an imperforate web or thermoplastic film to form a backsheet for a disposable diaper having breathable side edges. Fragmentary side edge portions of exemplary such lap-seamed laminates comprising laminae having overlapping side edges are illustrated in FIGS. 5, 6 and 7 albeit neither lamina is shown to be perforated in those figures. In an exemplary embodiment of the invention, cylinder 22 is steel, and has a diameter of about 11.4 inches (about 29 cm.).

Anvil cylinder 24, FIG. 1, is preferably a smooth surfaced, right circular cylinder of steel. In an exemplary embodiment of the invention, anvil cylinder 24 has a 4.5 inch (about 11.4 cm.) diameter, and is independently power rotated by a speed controlled direct current motor.

Means 26, FIG. 2, for biasing patterned cylinder 22 towards anvil cylinder 24 comprises pressure regulating means 55, and pneumatic actuator means 56. Pressure regulating means 55 is adapted to have its inlet connected to a supply source P of pressurized air, and to have its outlet connected to pneumatic actuator means 56 in order to adjust and control the pneumatic actuator means loading of cylinders 22 and 24 towards each other. Whereas only one pneumatic actuator or means 56 is visible in FIG. 1, identical actuators are in fact connected to each end journal of the cylinder; and, of course, each end journal is supported by frame members and ancillary hardware (not shown) to be vertically moveable so that, in fact, the pressure biasing means can be effective.

Drive means 28, and drive means 29, FIG. 1, are provided to independently drive cylinders 22 and 24, respectively. Thus, they constitute means for power rotating the cylinders so that there is a predetermined but adjustable relationship between their surface velocities. This can be synchronous, or assynchronous: equal surface velocities; or with a predetermined surface velocity differential with either cylinder being driven faster than the other. In an exemplary embodiment that is integrated into a disposable diaper converter, patterned cylinder 22 is driven by the converter line drive through a gear train so that its surface velocity is essentially matched to the line velocity of the converter; and, as stated above, anvil cylinder 24 is powered by an independently speed controlled DC (direct current) drive. This enables adjusting the surface velocity of the anvil cylinder to be equal to, or less than, or greater than the surface velocity of the patterned cylinder by predetermined amounts or percentages.

Temperature control means 30a and 30b, FIG. 1, are provided to adjustably control the surface temperatures of cylinders 22 and 24, respectively. As stated above, these means enable independently heating each of the cylinders 22 and 24 to establish surface temperatures thereon that are predetermined degrees below the melt temperature of the thermoplastic lamina disposed most adjacent to each. As also stated above, such heating enables effecting thermobonding of the lamina at lower nip biasing pressure than would otherwise be required for any given line speed and surface velocity differential between cylinders 22 and 24; and obviates having the laminae melting and sticking to the cylinders during, for example, converter and/or laminator stops.

Rolls 31 through 38, inclusive, are provided for guiding and advancing webs or laminae 41 and 42, and laminate 45 through and away from nip 43. Preferably these rolls are driven at surface velocities which maintain predetermined levels of tension or stretch so that neither slack web conditions nor excessively tensioned/stretched webs and or laminate precipitate undesirable deleterious consequences. For example, in an exemplary disposable diaper converter comprising the present invention, rolls 31 through 38, and cylinder 22 are driven through gear trains and the like from the main converter drive to provide a nominal draw of about one percent in the lengths of webs 41 and 42 being forwarded to nip 43 from the S-wrap roll pairs 31/32 and 33/34 for web forwarding control purposes; and about an equal amount of additional draw in the length of laminate 45 being forwarded from nip 43 by the S-wrap drive rolls 37 and 38.

Figure 3:
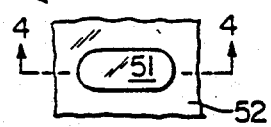
FIG. 3 is an enlarged scale, fragmentary view looking radially inwardly toward a pattern element—a bonding lug—which is disposed on the cylindrical surface of the patterned cylinder shown in FIG. 2.
Figure 4:
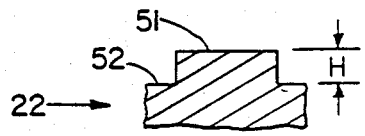
FIG. 4 is a fragmentary sectional view taken along section line 4—4 of FIG. 3.

Turning now to FIG. 3, a fragmentary portion of cylinder 22 is shown which comprises one pattern element 51 disposed on cylindrical surface 52. FIG. 4, a fragmentary sectional view taken along section line 4—4 of FIG. 3, shows that the pattern element 51 is an integral portion of cylinder 22, has substantially vertical side surfaces, and projects radially outwardly a distance H: ie, the radial height of the pattern element. While such an integral relationship is preferred, it is not intended to thereby limit the present invention to such integral constructions. In an exemplary apparatus 20, pattern element 51 has an oval planform having a width of about 0.055 inch (about 0.14 cm.), length of about 0.086 inch (about 0.22 cm.), end radii of about 0.0275 inch (about 0.07 cm.), end areas of about 0.004 square inches (about 0.026 square centimeters) and are oriented on the surface of cylinder 22 with their width dimensions extending circumferentially. Starting with a right circular cylinder, pattern elements 51 were machined by removing surrounding metal by electric discharge machining to a depth of from about 0.015 to about 0.020 inch (about 0.4 mm to about 0.5 mm). Additionally, they were spaced—center to center—about 0.0/0 inch circumferentially (ie, in the machine direction), and about 0.072 inch laterally (ie, in the cross machine direction). A variation of such an element has a slightly chamfered edge: ie, about 0.010 inch wide edge portion beveled at about forty-five degrees.

FIG. 5 is a plan view of a fragmentary portion of laminate 45, FIG. 1, comprising overlapping edge portions of laminae 41 and 42 which have been thermobonded together by a pattern of bond sites 51b: the pattern being the pattern of pattern elements which extends circumferentially about one end of pattern cylinder 22, FIG. 2. For clarity, the machine direction oriented edges of laminae 41 and 42 are designated 41e and 42e, respectively, in FIG. 5.

FIG. 6, is a somewhat schematic, fragmentary sectional view taken along section line 6—6 of FIG. 5, which illustratively shows a bond site 51b which thermobonds laminae 41 and 42 together to form laminate 45. As shown, the bond site 51b has a bottom surface 51bb; substantially vertical side walls 53 and 54; and shows the top surface of the bond site to be recessed substantially further below the top surface of web 51 than the bottom surface 51bb is recessed from the bottom surface of web 42. While not wishing to be bound by a theory of operation, it is believed that such recessing on the pattern-element side of laminate 45 may be precipitated by the pattern elements 51 displacing portions of the laminae per se; and the recessing on the anvil facing side of the laminate may be precipitated by cooling and removal of compressive forces upon laminate 45 upon its issuing from nip 43, FIG. 1. Indeed, in some lamina, portions of bond sites may even protrude rather than being recessed.

FIG. 7, a plan view of a fragmentary portion of an alternate laminate 145 made in accordance with the present invention. Laminate 145 is different from laminate 45 inasmuch as the zig zag pattern of bond sites of laminate 145 comprises only 3 bond sites per leg whereas the pattern of laminate 45, FIG. 5, comprises 5 bond sites per leg; and the bond sites of laminate 145 were precipitated by pattern elements similar to pattern elements 51, FIG. 4, but for having sloped sides rather than vertical sides. Thus, each bond site 151b of laminate 145 has tapered or filleted side walls 151f.

An exemplary embodiment of apparatus 20, FIG. 1, comprising the exemplary elements described above was operated as follows to make sample laminates comprising overlapping side edge portions of two thermoplastic laminae.

SAMPLE SET 1

A first set of samples—samples 1a, 1b, 1c, 1d, and 1e—comprising identical polyethylene laminae having nominal thicknesses of about one-and-two-tenths mil (about 0.03 mm), and melt temperatures of about 225 degrees Fahrenheit (about 107 degrees Celcius) were run at a constant line velocity of about four-hundred-fifty feet per minute (about 137 meters per minute); and with both nip defining cylinders heated to provide surface temperatures of about one-hundred-sixty degrees Fahrenheit (about 73 degrees Celcius). Four different anvil cylinder surface velocities were set: minus five, zero, five, ten, and twenty percent faster than the patterned cylinder/line velocity. At each differential velocity condition, the nip biasing pressure was adjusted to precipitate bonds having about equal nominal peel strengths. The results are tabulated in TABLE 1. Note that nip biasing air pressure (ie, the pressure adjusted by regulator 55, FIG. 1) values are included as well as calculated nominal pattern element loadings in pounds per square inch (psi). Without intending to thereby limit the present invention, it is believed that the relative values of pressure (ie, their differences) manifest a principal benefit of the invention: that substantially lower pressures can be used in combination with greater velocity differentials to achieve bonds having approximately the same nominal peel strengths. This benefit translates, of course, into substantially longer pattern element lives.

TABLE 1

| Sample No. | Differential Velocity, Anvil Cylinder Faster Than Patterned Cyl. | Nip Biasing Actuating Cylinders, psi | Calculated Pattern Element Loading, kpsi | Relative Peel Strength |
|---|---|---|---|---|
| 1a | −5% | 40 | 90 | 475 |
| 1b | 0% | 50 | 113 | 500 |
| 1c | 5% | 40 | 90 | 475 |
| 1d | 10% | 30 | 68 | 475 |
| 1e | 20% | 20 | 45 | 450 |

Generally speaking, TABLE 1 illustrates that nip biasing pressure and differential velocity are inversely related. That is, all other things being equal, nip biasing pressure may be reduced as differential velocity is increased. Thus, nip biasing pressure may be set at values below the yield point of the pattern elements to assure relatively long operating lives for the pattern elements.

SAMPLE SET 2

A second set of samples—samples 2a, 2b, 2c, and 2d—were run using the same laminae as for sample Set No. 1 at constant nip biasing cylinder pressure of about 40 psi (ie, a calculated pattern element value of about 90,000 psi); and with the cylinders still heated to one-hundred-sixty degrees Fahrenheit. At four selected line velocities, the velocity differential was adjusted to precipitate bonds having about equal nominal peel strengths. The resulting data are tabulated in TABLE 2.

TABLE 2

| Sample No. | Line Velocity, Feet Per Minute | Differential Velocity, Anvil Cylinder Faster Than Patterned Cylinder | Relative Peel Strength |
|---|---|---|---|
| 2a | 450 | 20% | 620 |
| 2b | 600 | 10 | 600 |
| 2c | 675 | 5% | 580 |
| 2d | 900 | 0 | 630 |

Generally speaking, TABLE 2 illustrates that line velocity and differential velocity are inversely related. That is, all other things being equal, as line speed increases, lower or no differential velocity is required to achieve a given nominal level of bond peel strength. Additionally, while peel strength data were taken in grams per inch units, only relative values are listed in the tables inasmuch as different test methodologies may precipitate different values.

SAMPLE SET 3

A third set of samples—Samples 3a, 3b, 3c, 3d, and 3e—were laminated from the same laminae as Sample Sets 1 and 2 above, using zero differential velocity, and heating both nip defining cylinders to about one-hundred-eighty degrees Fahrenheit (about 82 degrees Celcius). Five values of line velocity were set; then, the nip biasing pressure was adjusted to precipitate bonds having about equal nominal peel strengths. The resulting data are tabulated in TABLE 3.

TABLE 3

| Sample No. | Line Velocity Feet Per Minute | Biasing Actuating Cylinders, psi | Calculated Pattern Element Loading, kpsi | Relative Peel Strength |
|---|---|---|---|---|
| 3a | 100 | 70 | 158 | 420 |
| 3b | 170 | 50 | 113 | 460 |
| 3c | 300 | 50 | 113 | 470 |
| 3d | 450 | 40 | 90 | 450 |
| 3e | 600 | 30 | 68 | 450 |

Generally speaking, these data illustrate that—in the absence of differential velocity between the nip defining cylinders—the amount of nip biasing pressure required decreases as line velocity increases: particularly above three-hundred feet per minute (about 91.4 meters per minute); and, more particularly, at and above about four-hundred-fifty feet per minute (about 137 meters per minute).

The relation between line velocity and pattern element loading is linear and inverse for line speeds of 300 to 600 feet per minute. The relation is approximated by the formula: $PEL = -0.15LV + 158$, where PEL is a pattern element loading in kpsi, LV is the line velocity in feet per minute and $300 \leq LV \leq 600$.

Reflecting back to TABLES 1, 2 and 3, they essentially resulted from exploring three parameters two at a time: nip biasing pressure, velocity differential between the defining cylinders, and line velocity. Another important variable with respect to this invention is the temperature(s) to which the surfaces of the nip defining members (ie, their surfaces) are heated. Generally speaking, all other things being equal, as cylinder temperature is increased from ambient towards the melting temperature of the thermoplastic lamina disposed closest to or in contact with the cylinder, bonds of increasing strength will be realized up to a point; and further increases in cylinder temperatures will produce bonds of lesser strength. In general, cylinder surface temperatures in the range of from about forty to about one-hundred degrees Fahrenheit below the melt temperature of the lamina disposed closest to or in contact with each respective nip defining cylinder produce high strength bonds, and without precipitating holes in the laminae. Directionally, optimum cylinder surface temperatures are inversely related to line velocity: higher cylinder temperatures being preferred at relatively slow line velocities, and lower cylinder temperatures being preferred at relatively high line velocities. Thus, for example, with the identical laminae (both polyethylene having a melting temperature of about two-hundred-twenty-five degrees Fahrenheit) as utilized for Sample Sets 1, 2, and 3, satisfactory bond strengths—all other things being equal—were achieved at cylinder temperatures of about one hundred-forty degrees Fahrenheit (about 60 degrees Celcius) at a line velocity of about six-hundred feet per minute (about 183 meters per minute). When one lamina was replaced with a higher melting point polyethylene—a film having a melting point of about two-hundred-fifty-seven degrees Fahrenheit (about 125 degrees Celcius)—comparable strength bonds were achieved by heating the cylinder in contact with that lamina to a temperature of about one-hundred-seventy degrees Fahrenheit (about 77 degrees Celcius).

While not wishing to be bound by a theory of operation, it is believed that differential velocity—when used—contributes shear energy to enable dynamic, mechanically induced, thermobonding. This is in addition to heat generated from molecular flow/fluid friction as bond-site thermoplastic is quickly displaced by the intrusion of pattern elements into the thermoplastic laminae. Additionally, inasmuch as effective bonding of webs or laminae occurs when they are at room ambient temperature going into the nip, it is believed that heating the nip defining members (eg, cylinders 22 and 24) acts more to retard heat flow from the bond sites rather than being a source of heat flow into the bond sites. Moreover, inasmuch as maximum bond strengths are normally achieved at cylinder temperatures well below the melt temperatures of the laminae, it is believed that bonds made at higher temperatures do not wholly set as the laminate is forwarded from the bonding nip. Indeed, at high line speeds, good bonding may be achieved without heating the cylinders; ie, having the cylinders at room ambient temperature.

While specific examples have been described above, generally speaking, velocity differentials in the range of from about 2 to about 40 percent are preferred; from about 2 to about 20 percent are more preferred; and the surface velocity of the anvil cylinder is preferably greater than the pattern cylinder albeit it is not intended to thereby limit the present invention. Additionally, while it is preferred that the anvil cylinder have a smooth cylindrical surface, it is also not intended to thereby limit the invention to a laminating apparatus comprising a smooth surfaced anvil cylinder. Moreover, while the invention has been discussed above through the use of two laminae in continuous length web forms, it is not intended to thereby limit the invention to either continuous laminae or to two laminae. That is, discontinuous discrete lengths of lamina can also be laminated through application of this invention; and, of course, greater than two laminae may be laminated through application of this invention.

Referring back to FIG. 4, pattern element 51 is shown to have a height H. Generally speaking, bond sites of minimum thickness are obtained when H is greater than the sum of the thicknesses of the laminae being laminated: eg, the sum of the thicknesses of laminae 41 and 42 for the examples described above. Such dimensioned pattern elements generally precipitate bond sites having nominal thicknesses of about one-half mil (about 0.0127 mm) when the laminae have nominal thicknesses of about one mil each. In the event thicker bond sites are desired, the pattern elements must have heights which are about equal to or sufficiently less than the sum of the thicknesses of the laminae to precipitate bond sites having the desired thicknesses.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A method of dynamically bonding plural lamina together, at least one of which laminae comprises thermoplastic material, said method comprising the steps of:
   forwarding said laminae at a velocity of about 300 to about 600 per feet minute, with portions thereof in face to face relation, through a pressure biased nip between a relief patterned nip defining member having pattern element segments, and a nip defining anvil member;
   biasing said nip defining members towards each other with a predetermined pattern-element loading that is between about 68,000 psi and about 113,000 psi; and
   sufficiently heating each said nip defining member to enable dynamically thermobonding said laminae together.

2. The method of claim 1 wherein said laminae are forwarded at a velocity of about 450 feet per minute or greater.

3. The method of claim 1 wherein the step of heating comprises heating each said nip defining member to provide a surface temperature that will precipitate relatively high strength bonds, said temperature being inversely related to line velocity and directly related to the melt temperature of the thermoplastic lamina disposed most adjacent thereto.

4. The method of claim 1 wherein said step of heating of each said nip defining member having a direct contacting relation with a thermoplastic lamina being limited to effecting a surface temperature that is sufficiently below the melt temperature of the thermoplastic lamina in direct contacting relation therewith to substantially preclude the thermoplastic from melting or sticking to the nip defining members in the event the nip defining members are stopped.

5. The method of claim 1 wherein said pattern element segments are discrete projections having tip surface areas greater than about 0.002 square inches.

6. The method of claim 1 wherein said pattern element segments are discrete projections having tip surface areas of about 0.004 square inches or greater.

7. The method of claim 1 or 2 wherein said nip defining members are driven at substantially equal surface velocities.

8. The method of claim 1 or 2 wherein said nip defining members are driven at differential surface velocities within a predetermined range.

9. The method of claim 1 wherein:
said nip defining members are biased towards each other with a predetermined pattern-element loading that is approximated by the formula: $PEL = -0.15LV + 158$, where PEL is the pattern element loading in kpsi, LV is the line velocity in feet per minute and $300 \leq LV \leq 600$; and
each said nip defining member is sufficiently heated to a temperature less than the melting temperature of the laminae to enable dynamically thermobonding said laminae together.

* * * * *

UNITED STATES PATENT AND TRADEMARK OFFICE
CERTIFICATE OF CORRECTION

PATENT NO. : 4,919,738

DATED : April 24, 1990

INVENTOR(S) : W. Kenneth Ball, David J. K. Goulait and James E. Zorb

It is certified that error appears in the above-identified patent and that said Letters Patent is hereby corrected as shown below:

ON TITLE PAGE:

[56] References Cited

U.S. PATENT DOCUMENTS
delete "4,248,878  11/1985" and insert therefor --4,624,878  11/1986--

Attorney, Agent, or Firm - reads "Frederick H. Braun" should read --Fredrick H. Braun--.

[57] ABSTRACT: line 23, reads "closet" should read --closest--.

Column 1, line 56, reads "0.005" should read --0.0005--.

Column 6, line 61, reads "51" should read --41--.

Signed and Sealed this

Third Day of December, 1991

Attest:

HARRY F. MANBECK, JR.

*Attesting Officer*   *Commissioner of Patents and Trademarks*